United States Patent
Youn et al.

(10) Patent No.: US 11,672,854 B2
(45) Date of Patent: Jun. 13, 2023

(54) MULTIVALENT LIVE INFLUENZA VACCINE PLATFORM USING RECOMBINANT ADENOVIRUS

(71) Applicants: INJE UNIVERSITY INDUSTRY-ACADEMIC COOPERATION FOUNDATION, Gimhae-si (KR); GENEUIN-TECH CO., LTD., Gimhae-si (KR)

(72) Inventors: Hyun Joo Youn, Gimhae-si (KR); Eun Yeong Han, Seoul (KR)

(73) Assignees: INJE UNIVERSITY INDUSTRY-ACADEMIC COOPERATION FOUNDATION, Gimhae-si (KR); GENEUIN-TECH CO., LTD., Gimhae-si (KR)

( * ) Notice: Subject to any disclaimer, the term of this patent is extended or adjusted under 35 U.S.C. 154(b) by 96 days.

(21) Appl. No.: 16/980,838

(22) PCT Filed: Jan. 16, 2019

(86) PCT No.: PCT/KR2019/000651
§ 371 (c)(1),
(2) Date: Sep. 14, 2020

(87) PCT Pub. No.: WO2019/177256
PCT Pub. Date: Sep. 19, 2019

(65) Prior Publication Data
US 2021/0361763 A1  Nov. 25, 2021

(30) Foreign Application Priority Data
Mar. 14, 2018 (KR) ............ 10-2018-0029823

(51) Int. Cl.
*A61K 39/145* (2006.01)
*A61P 31/16* (2006.01)
*C12N 15/86* (2006.01)
*C07K 14/005* (2006.01)
*A61K 39/00* (2006.01)

(52) U.S. Cl.
CPC ............ *A61K 39/145* (2013.01); *A61P 31/16* (2018.01); *C07K 14/005* (2013.01); *C12N 15/86* (2013.01); *A61K 2039/543* (2013.01); *A61K 2039/552* (2013.01); *A61K 2039/70* (2013.01)

(58) Field of Classification Search
None
See application file for complete search history.

(56) References Cited
U.S. PATENT DOCUMENTS 8,043,856 B2  10/2011  Kawaoka et al.
2009/0324644 A1*  12/2009  Ramos ............... A61K 39/12
424/209.1

FOREIGN PATENT DOCUMENTS

| CN | 102719479 A | 10/2012 |
|---|---|---|
| KR | 10-2015-0104117 A | 9/2015 |
| KR | 10-1835989 B1 | 3/2018 |
| WO | 2014-099931 A1 | 6/2014 |
| WO | 2017/218624 A1 | 12/2017 |

OTHER PUBLICATIONS

Li et al., Influenza Viral Vectors Expressing Two Kinds of HA Proteins as Bivalent Vaccine Against Highly Pathogenic Avian Influenza Viruses of Clade, 2018, Frontiers in Microbiology, vol. 9, article 604.*
International Search Report for PCT/KR2019/000651 dated May 10, 2019 from Korean Intellectual Property Office.
NCBI, GenBank accession No. KC172926.1 (Feb. 23, 2015).
NCBI, GenBank accession No. CY035491.1 (Jul. 26, 2016).
NCBI, GenBank accession No. AAK38298.1 (Apr. 19, 2001).
Surender Khurana et al., "H5 N-terminal β sheet promotes oligomerization of H7-HA1 that induces better antibody affinity maturation and enhanced protection against H7N7 and H7N9 viruses compared to inactivated influenza vaccine", Vaccine, vol. 32, Issue 48, Nov. 12, 2014, pp. 6421-6432.
M. M. Shmarov et al., "Induction of a Protective Heterosubtypic Immune Response Against the Influenza Virus by using Recombinant Adenoviral Vectors Expressing Hemagglutinin of the Influenza H5 Virus", Acta Naturae, vol. 2, No. 1(4), 2010, pp. 111-118.
Florian Krammer et al., "Advances in the development of influenza virus vaccines", Nature Reviews Drug Discovery, vol. 14, Mar. 2015, pp. 167-182.
Yufei Tian, "Construction and Immune Efficacy of HA gene expression Against HAPIV", China Master's Theses Fulltext Database (Electronic Journal) Agricultural Science and Technology Series, No. 2008/10.

* cited by examiner

*Primary Examiner* — Benjamin P Blumel
(74) *Attorney, Agent, or Firm* — Revolution IP, PLLC

(57) ABSTRACT

The present invention relates to a multivalent live influenza vaccine platform using a recombinant adenovirus. The present invention is a live attenuated vaccine platform using a recombinant virus and it is easy to inoculate because it is infected with the respiratory tract like influenza virus and exhibits a vaccine action and it is a multivalent vaccine which combines two types into one and it is a highly novel vaccine that does not need to mix viruses compared to vaccines using multiple combinations of one vaccine. The present invention is the first vaccine in which a gene obtained by fusion of two influenza antigen genes into one gene is incorporated into a recombinant virus. Instead of using the entire HA gene of influenza, but using a structurally independent HA1 gene, which is about half of the total HA gene, several types of HA genes could be fused into one. When the recombinant virus was inoculated into mice by nasal inhalation, it was confirmed that it is an effective vaccine in which the vaccine effect is induced by two inoculations, and the vaccine platform of the present invention is expected to be useful for the development of a vaccine for human influenza infection.

9 Claims, 3 Drawing Sheets

Specification includes a Sequence Listing.

| Leader | HA1(H5 type) | Linker | HA1(H7 type) | Flag/His |

(B)

MEKIVLLLAIVSLVKSDQICIGYHANNSTEQVDTIMEKNVTVTHAQDILEKTHNGKLC
DLNGVKPLILRDCSVAGWLLGNPMCDEFINVPEWSYIVEKASPANDLCYPGDFNDY
EELKHLLSRTNHFEKIQIIPKSSWSNHDASSGVSSACPYHGRSSFFRNVVWLIKKNS
AYPTIKRSYNNTNQEDLLVLWGIHHPNDAAEQTKLYQNPTTYISVGTSTLNQRLVPE
IATRPKVNGQSGRMEFFWTILKPNDAINFESNGNFIAPEYAYKIVKKGDSAIMKSELE
YGNCNTKCQTPMGAINSSMPFHNIHPLTIGECPKYVKSNRLVLATGLRNTPQRERRR
KKRGGGGSGGGGSGGGGSNADKICLGHHAVSNGTKVNTLTERGVEVVNATETVER
TNVPRICSKGKRTVDLGQCGLLGTITGPPQCDQFLEFSADLIIERREGSDVCYPGKFV
NEEALRQILRESGGIDKETMGFTYSGIRTNGATSACRRSGSSFYAEMKWLLSNTDNA
AFPQMTKSYKNTRKDPALIIWGIHHSGSTTEQTKLYGSGNKLITVGSSNYQQSFVPS
PEARPQVNGQSGRIDFHWLMLNPNDTVTFSFNGAFIAPDRASFLRGKSMGIQSGVQ
VDANCEGDCYHSGGTIISNLPPQNIMSRAVGKCPRYVKQESLLLATGMKNVPEIPKG
RDYKDDDDKHHHHHH (SEQ ID NO: 1)

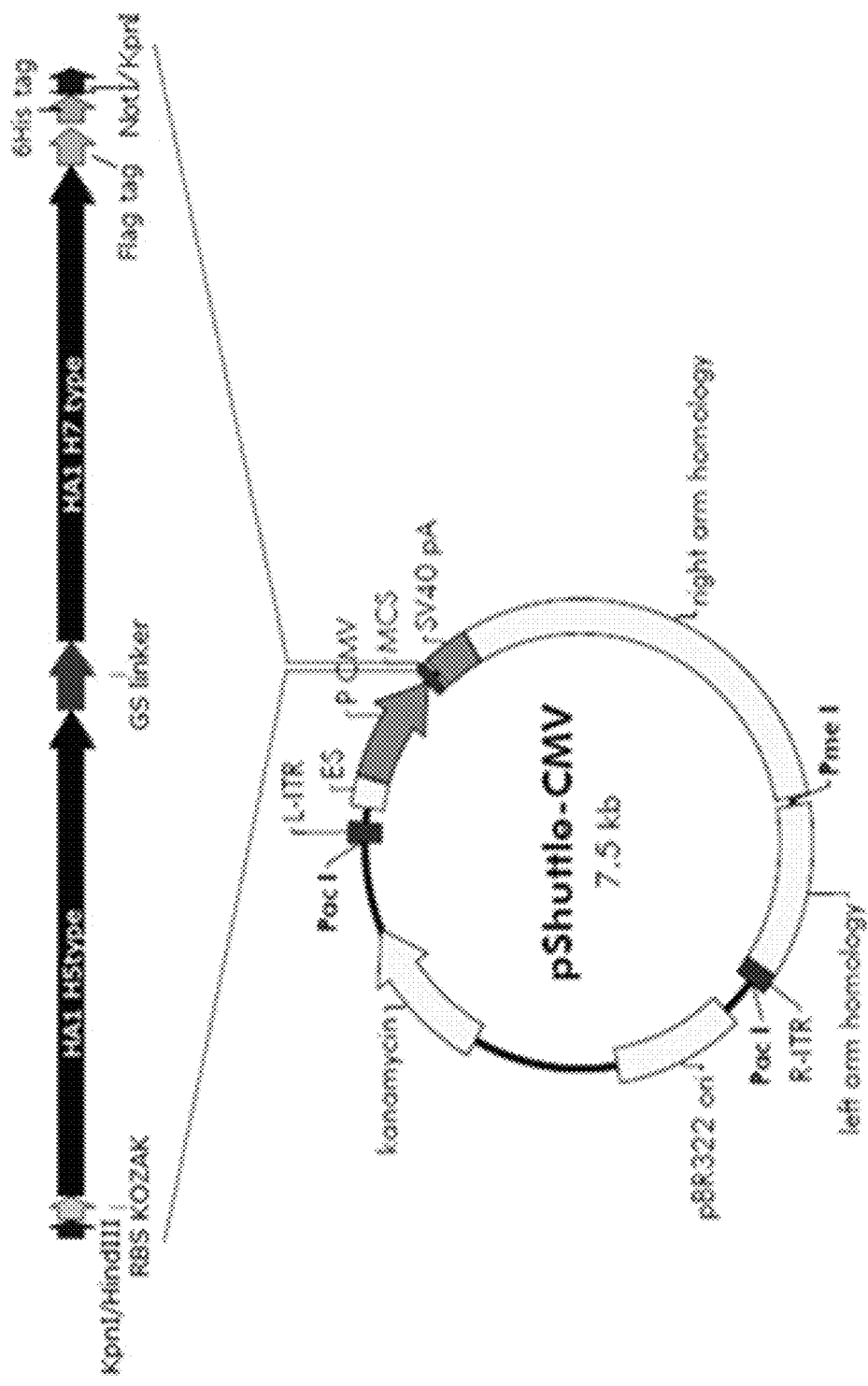
[FIG. 2]

[FIG. 3]
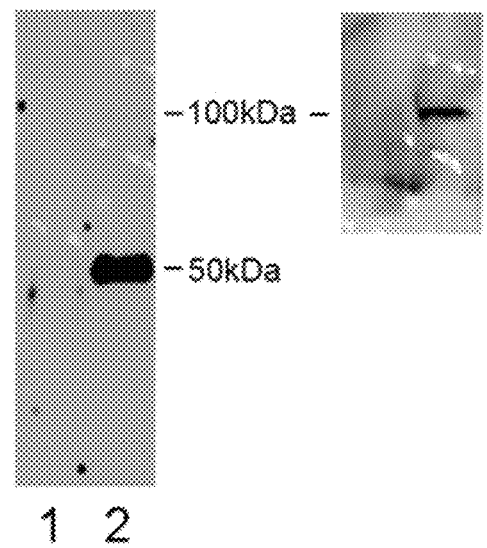
[FIG. 4]
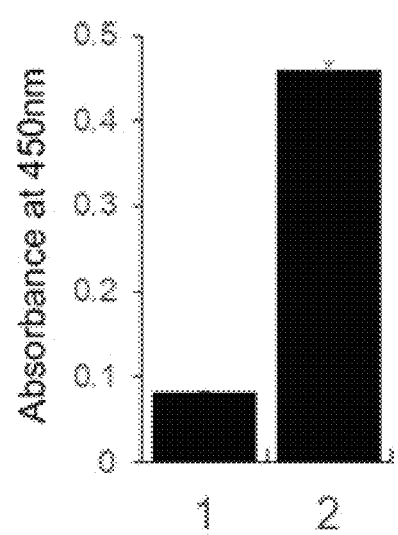

MULTIVALENT LIVE INFLUENZA VACCINE PLATFORM USING RECOMBINANT ADENOVIRUS

TECHNICAL FIELD

The present invention relates to a multivalent live influenza vaccine platform using a recombinant adenovirus and specifically, to avian influenza (AI virus) live vaccine using a recombinant adenovirus, wherein a vaccine candidate material capable of simultaneously defending against H5 type and H7 type highly pathogenic avian influenza virus is developed and prepared by linking the vaccine candidate material harmless to the human body to an adenovirus.

BACKGROUND ART

Influenza or flu is a respiratory disease caused by infection with the influenza virus, and has symptoms such as chills, fever, sore throat, muscle pain, headache, and cough when infected, and in severe cases, it causes fatal complications such as fulminant pneumonia. Human or avian influenza is caused by the influenza A virus, and spreads worldwide in a short time through wild birds and travelers, causing pandemic outbreaks. Avian influenza (AI) is a type of influenza A virus, an amorphous RNA virus with an envelope. Influenza A virus is an amorphous virus with an envelope belonging to the Orthomyxoviridae family and is a virus whose genes are composed of 8 segmented RNA genomes. This virus is transformed into various types by means of mutations or recombination or mixing of genome fragments, causing a new type of influenza epidemic every year, and it also causes pandemic outbreak with a cycle of about 10 years. Influenza virus infects and proliferates in various host cells such as humans, birds and pigs to produce large amounts of viral particles. Because of these characteristics, influenza viruses often have a new type of influenza virus that has changed its infectious host through gene exchange between species.

The types of influenza viruses are so diverse that new types of viruses appear whenever an epidemic occurs. Three types of influenza viruses are known, A, B, and C, but most human or avian influenza epidemics are caused by influenza A virus. Influenza A virus is classified into various H-type and N-type depending on the antigenicity of HA and NA proteins of envelope, and H5N1 and H7N9 types are representative highly pathogenic AI viruses. Influenza virus is very active in type conversion due to gene mutations during the genome duplication process or recombination or mixing of genome fragments with other types of viruses, and through such a process, a new influenza epidemic is occurring. In addition, since influenza viruses are infected with various animals such as humans, birds and pigs and gene exchange between species is possible, when an AI virus is transfected to humans, it is highly likely that the AI virus will be converted to human influenza virus through type change. For example, in the case of swine flu that occurred in 2009, it is a new influenza virus obtained through recombination of genome fragments while influenza A virus infects human, avian, and swine host cells. The novel swine-origin influenza A occurred in 2009 is a new influenza virus obtained through recombination of segmented genome when influenza A virus infects human, avian, and swine host cells. In this regard, if the human infection of the Asian H5N1 and H7N9 avian influenza viruses in epidemic increases, the emergence of new human influenza viruses is possible.

AI viruses are classified into highly pathogenic avian influenza (HPAI) and low pathogenic avian influenza (LPAI) depending on the propagation rate, mortality rate, and human infection and the H5N1 and H7N9 types, which are currently prevalent in Asia, are representative HPAIs. Because these HPAIs cause the death of infected individuals and contagion spreads rapidly, and thus they are classified as Class 1 infectious disease in domestic animals of the Domestic Animal Infectious Disease Control Law and high-level infection control measures are applied to prevent human infection. AI viruses can be infected to humans by contacting the virus particles secreted by birds through the eye, nose or mouth or by inhaling the virus particles in the air. Human infection of the AI virus has evolved into a deadly human influenza virus that could cause a new human influenza pandemic. HPAI virus is a deadly infectious disease in the poultry industry because high-level precautions such as poultry stamping out are applied to prevent the risk of human infection due to the rapid contagion of HPAI virus and measures such as chicken consumption and import/export control are taken. In Korea, avian influenza (AI) has occurred several times in Korea since 2003, and in 2016, a highly pathogenic avian influenza (AI) was prevalent and large-scale stamping-out of poultry has been carried out. H5N1 and H7N9 types are Asian HPAI viruses, and because they show a very wide host range, human infection is possible. Human infection of these viruses has been reported repeatedly in China, and there remains a possibility of contagion to humans through poultry or migratory birds in Korea. The AI virus epidemic has been reported in Korea since 2003, and highly pathogenic avian influenza has spread since 2016 to have a fatal impact on the domestic poultry industry, up to now. Due to the avian influenza outbreak in the winter of 2016, 50 million chickens were killed for three months, and economic losses were incurred over 1.5 trillion won due to the sudden rise of egg prices, egg imports and the like.

The development of an effective and safe poultry vaccine is the surest way to avoid concerns of human contagion as well as economic losses to farmers. In particular, since it is difficult to predict which type of influenza virus will cause the AI epidemic, it is necessary to develop a multivalent vaccine that can prevent the contagion of various types of HPAI. In addition, as for the AI infectious disease vaccine, the development of a live vaccine is necessary, which can respond immediately in the event of a disease, can be produced in large quantities in a short period of time and have high immune effect and can be administered easily like respiratory vaccination. In addition, there is a need for an efficient multivalent vaccine that can be used prophylactically in areas where HPAI is not prevalent, and can prevent various HPAI viruses. Currently, as a multivalent vaccine, viruses obtained by culturing several types of viruses separately and mixing them are used. In this case, there are problems such as an imbalance in the composition of virus types in the vaccine and bias in immune response due to a specific type. In order to solve these shortcomings, to develop an AI vaccine which has high immune response and is easy to inoculate, it is urgent to develop a HPAI vaccine using a recombinant virus that produces various types of influenza antigens from one virus particle.

DISCLOSURE

Technical Problem

An object of the present invention is a recombinant expression vector comprising an influenza virus H5 type hemagglutinin 1 (HA1) gene and an influenza virus H7 type HA1 gene, a recombinant strain transformed with the recombinant expression vector, and a recombinant fusion protein of influenza virus H5 type HA1 and H7 type HA1, which is obtained from the recombinant strain.

Another object of the present invention is to provide a method of preparing a recombinant adenovirus particle comprising transfecting an adenovirus with the recombinant expression vector and a recombinant adenovirus particle prepared according to the method.

Another object of the present invention is to provide a vaccine composition for preventing or treating influenza comprising recombinant adenovirus particles as an active ingredient, and a method of preventing or treating influenza by administering the vaccine composition to individuals other than humans.

Technical Solution

In order to achieve the above object, the present invention provides a recombinant expression vector comprising an influenza virus H5 type hemagglutinin 1 (HA1) gene and an influenza virus H7 type HA1 gene.

Also, the present invention provides a recombinant strain transformed with the recombinant expression vector.

In addition, the present invention provides a recombinant fusion protein of influenza virus H5 type HA1 and H7 type HA1, which is obtained from the recombinant strain.

Furthermore, the present invention provides a method of preparing recombinant adenovirus particles comprising: transfecting adenovirus with recombinant expression vector; and culturing transfected adenovirus.

In addition, the present invention provides recombinant adenovirus particles prepared according to the above method.

In addition, the present invention provides a vaccine composition for preventing or treating influenza comprising the recombinant adenovirus particles as an active ingredient.

In addition, the present invention provides a method of preventing or treating influenza by administering the vaccine composition to individuals other than humans.

Advantageous Effects

The present invention relates to a multivalent live influenza vaccine platform using a recombinant adenovirus. The present invention is a live attenuated vaccine platform using a recombinant virus and it is easy to inoculate because it is infected with the respiratory tract like influenza virus and exhibits a vaccine action. It is a multivalent vaccine which combines two types into one and it is a highly novel vaccine that does not need to mix viruses compared to vaccines using multiple combinations of one vaccine. The present invention is the first vaccine in which a gene obtained by fusion of two influenza antigen genes into one gene is incorporated into a recombinant virus. Instead of using the entire HA gene of influenza, but using a structurally independent HA1 gene, which is about half of the total HA gene, several types of HA genes could be fused into one. When the recombinant virus was inoculated into mice by nasal inhalation, it was confirmed that it is an effective vaccine in which the vaccine effect is induced by two inoculations, and the vaccine platform of the present invention is expected to be useful for the development of a vaccine for human influenza infection.

DESCRIPTION OF DRAWINGS

FIG. 1 shows the structure (A) and amino acid sequence (B) of the H5 type HA1 and H7 type HA1 fusion protein. H5 type HA1(1-334)-linker (335-349)-H7 type HA1(350-572) was linked to the amino terminal in the order and Flag tag peptide is linked to 573-581, and a His tag peptide is linked to 582-587.

FIG. 2 shows the structure of the shuttle vector for adenovirus fabrication (pAd5-AI #4212) capable of expressing the H5 type HA1 and H7 type HA1 fusion proteins. The fabricated fusion protein gene was inserted between the CMV promoter of the pShuttle-CMV shuttle vector and the SV40 polyA site in a direction capable of transcribing the gene.

FIG. 3 shows the expression results of H5 type HA1 and H7 type HA1 fusion proteins. Lane 1: cell culture medium infected with control GFP-expressing recombinant adenovirus, lane 2: cell culture medium infected with fusion protein-expressing recombinant adenovirus (pAd5-AI #4212 adenovirus).

FIG. 4 shows the results of anti-HA antibody production in the blood of mice inoculated with multivalent live recombinant adenovirus vaccine through nasal inhalation. 1: serum of mice inhaled with GFP-expressing recombinant adenovirus as a control, 2: serum of mice inhaled with recombinant adenovirus expressing H5 type and H7 type HA1 fusion protein

BEST MODE

Accordingly, the present inventors used a gene in which H5 type and H7 type HA genes were fused into one gene for vaccine production in order to prepare a recombinant adenovirus vaccine against HPAI of H5 and H7 types. The HA protein of the influenza virus is a protein that acts as a receptor when the virus infects host cells, and consists of an HA1 portion and an HA2 portion. Even if these two parts are separated from each other, they maintain an independent structure without any modification of their structure in the HA protein, and the HA1 part alone can bind to the host cell receptor. Based on these points, a fusion gene was prepared by combining two reduced H5 type and H7 type HA1 genes into one gene. By linking two H5 and H7 HA1 genes into one gene, the overall gene size is not excessively large, so a recombinant adenovirus containing the fused gene can be produced and this recombinant virus can be used as a multivalent live influenza vaccine to complete the present invention.

The present invention provides a recombinant expression vector comprising an influenza virus H5 type hemagglutinin 1 (HA1) gene and an influenza virus H7 type HA1 gene.

Preferably, the recombinant expression vector may comprise a ribosome binding site, an influenza virus H5 type HA1 gene, a linker, an influenza virus H7 type HA1 gene and a tag gene in order, but it is not limited thereto.

More preferably, the influenza virus H5 type HA1 gene may be represented by SEQ ID NO: 2, and the influenza virus H7 type HA1 gene may be represented by SEQ ID NO: 3, but they are not limited thereto.

More preferably, the ribosome binding site may be RBS/Kozak (aaggaggccgccacc) to help the protein decoding, and the linker may be glycine/serine linker peptide, as a role of serving to link two genes for expression, and, and the tag gene may be a Flag tag (DYKDDDDKG) and His tag (HHHHHH) genes, as a role of serving to facilitate purification of the protein for expression, but they are not limited thereto.

More preferably, the influenza virus may be an influenza A virus, but it is not limited thereto.

In the present invention, "hemagglutinin (HA)" is one of the surface glycoproteins of influenza virus and mediates viral-cell membrane fusion during adhesion of the virus to host cells and cell penetration of the virus. It is a surface antigen protein of influenza virus that determines antigen specificity.

In the present invention, "vector" refers to a DNA molecule that replicates itself and is used to carry a clone gene (or other fragment of clone DNA).

In the present invention, "expression vector" refers to a recombinant DNA molecule comprising a target coding sequence and an appropriate nucleic acid sequence essential for expressing a coding sequence operably linked in a specific host organism. The expression vector may preferably contain at least one selectable marker. The marker is typically a nucleic acid sequence having a property that can be selected by a chemical method, and includes all genes capable of distinguishing a transformed cell from a non-transformed cell. Examples include antibiotic resistance genes such as Ampicillin, Kanamycin, Geneticin (G418), Bleomycin, Hygromycin, and Chloramphenicol, but it is limited thereto, and can be appropriately selected by a person skilled in the art.

In order to express the DNA sequence of the present invention, any of a wide variety of expression regulatory sequences can be used in the vector. Examples of useful expression regulatory sequences may include, for example, early and late promoters of SV40 or adenovirus, promoters and enhancers of CMV, LTR of retroviruses, lac system, trp system, TAC or TRC system, T3 and T7 promoters, main operator and promoter region of phage lambda, the regulatory region of the fd code protein, the promoter for 3-phosphoglycerate kinase or other glycolase, the promoters of the phosphatase such as Pho5, alpha-crossing system promoters of yeast and constructs and other induced sequences known to regulate the expression of genes of prokaryotic or eukaryotic cells or their viruses, and various combinations thereof.

In addition, the present invention provides a recombinant strain transformed with the recombinant expression vector. Preferably, the recombinant strain may be an adenovirus, but it is not limited thereto.

In addition, the present invention provides a recombinant fusion protein of influenza virus H5 type HA1 and H7 type HA1, which is obtained from the recombinant strain.

Preferably, the recombinant fusion protein may be represented by SEQ ID NO: 1, but it is not limited thereto.

In the present invention, "fusion protein" means that one or more polypeptides are bound to a single strand of polypeptide through a peptide bond, and it refers to a fusion protein prepared by fusion of one or more genes including a target gene by a recombinant method and translation into a single polypeptide. In the present invention, the fusion protein may include an amino acid cleavage sequence (chemical materials or enzyme specific cleavage sequence) which can be cleaved by specifically recognizing by a chemical substance or enzyme between proteins or peptide sequences of interest which are fused to each other.

In addition, the present invention provides a method of preparing recombinant adenovirus particles comprising: transfecting adenovirus with recombinant expression vector; and culturing transfected adenovirus. Preferably, the recombinant adenovirus particles may express a recombinant fusion protein of influenza virus H5 type HA1 and H7 type HA1. More preferably, the recombinant fusion protein may be represented by SEQ ID NO: 1, but it is not limited thereto.

Furthermore, the present invention provides recombinant adenovirus particles prepared according to the above method.

In addition, the present invention provides a vaccine composition for preventing or treating influenza comprising the recombinant adenovirus particles as an active ingredient.

Host animals capable of causing an immune response by the vaccine of the present invention may include humans, dogs, cats, pigs, horses, chickens, ducks, turkeys, ferrets, etc., and preferably, the influenza may be avian influenza, swine influenza or human influenza, but it is not limited thereto.

The vaccine of the present invention may be an attenuated live vaccine or killed vaccine, a subunit vaccine, a synthetic vaccine or a genetic engineering vaccine, but live vaccines that induce an effective immune response are preferred.

In the present invention, the term “live vaccine” or “live attenuated vaccine” refers to a vaccine containing a live viral active ingredient. In addition, “attenuation” means that the toxicity of a living pathogen is artificially weakened, and it does not cause disease in the body by mutating genes involved in the essential metabolism of pathogens, but only stimulates the immune system to induce immunity. Viral attenuation can be achieved by ultraviolet (UV) irradiation, chemical treatment, or high-order continuous subculture in vitro. Attenuation can also be achieved by making clear genetic changes, for example by specific deletions of viral sequences known to provide toxicity or by insertion of sequences into the viral genome.

In addition, the vaccine of the present invention may further contain at least one selected from the group consisting of a solvent, an adjuvant and an excipient. Examples of the solvent include physiological saline or distilled water, and examples of immune enhancing agents include Freund’s incomplete or complete adjuvant, aluminum hydroxide gel and vegetable and mineral oils, and excipients include aluminum phosphate, aluminum hydroxide, or aluminum potassium sulfate, but they are not limited thereto, and may further include a material used in the preparation of a vaccine, well known to those skilled in the art.

In addition, the vaccine of the present invention may be prepared in an oral or parenteral formulation, and may be administered by intradermal, intramuscular, intraperitoneal, nasal or epidural routes.

Furthermore, the present invention provides a method of preventing or treating influenza by administering the vaccine composition to individuals other than humans.

In the present invention, “individual” means all animals, including humans, who have already been infected with or can be infected with influenza virus. The disease can be efficiently prevented and treated by administering the vaccine composition of the present invention to an individual. For example, the composition of the present invention can treat humans infected with various influenza virus subtypes or variants of influenza virus. In addition, the composition of the present invention can treat chickens or pigs infected with various influenza virus subtypes or variants of avian influenza. The composition of the present invention can be administered in combination with the conventional therapeutic agent for influenza virus infection disease.

In the present invention, “prevention” means any action of inhibiting or delaying the onset of influenza virus infection by administration of a vaccine composition. In addition, “treatment” refers to any action in which symptoms caused by influenza virus infection are improved or beneficially changed by administration of a vaccine composition.

The vaccine composition of the present invention is administered in a pharmaceutically effective amount. The term "pharmaceutically effective amount" means an amount sufficient to treat a disease with a reasonable benefit/risk ratio applicable to medical treatment, and the effective dose level may be determined by factors including the type and severity of the individual, age, sex, type of infected virus, drug activity, sensitivity to drugs, time of administration, route of administration, rate of excretion, treatment period, drugs used concurrently, and other factors well known in the medical field. The vaccine composition of the present invention may be administered as an individual therapeutic agent or administered in combination with other therapeutic agents, and may be administered sequentially or simultaneously with a conventional therapeutic agent. Also, it can be administered single or multiple. It is important to administer an amount capable of obtaining the maximum effect in a minimum amount without side effects in consideration of all the above factors, and can be easily determined by a person skilled in the art.

Hereinafter, the present invention will be described in more detail through examples. These examples are only intended to illustrate the present invention in more detail, and it will be apparent to those skilled in the art that the scope of the present invention is not limited by these examples according to the gist of the present invention.

<Example 1> Preparation of H5 Type and H7 Type HA1 Fusion Protein (H5/H7 Fusion Protein) Genes In order to secure the nucleic sequence of the H5 type HA1 gene, in amino acid sequences of the HA protein of the influenza A virus (A/goose/Guangdong/1/1996(H5N1)) isolated from goose in Guangdong, China in 1996 in Gene Bank Database (NC_007362.1), the amino acid sequences from amino terminals 1 to 346 corresponding to the HA1 region were selected. This amino acid sequence contains the leader peptide portion of the HA protein and the protein coding region of the portion corresponding to the HA1 region. This region contains the receptor-binding site and esterase part of the HA protein, but excludes fusion peptide, HA2 part, and transmembrane region. To secure the nucleic sequence of the H7 type HA1 gene, in amino acid sequence of the HA protein of the influenza A virus (A/Chicken/Italy/1067/99(H7N1)) isolated from Italian chickens in 1999 in the Gene Bank Database (AJ584647.1) amino acid sequences from amino terminals 17 to 339 corresponding to the HA1 region were selected. This region contains the receptor-binding site and esterase part of the HA protein, but excludes leader peptide part, fusion peptide, HA2 part, and transmembrane region. These two HA1 proteins were linked in the order of H5 type HA1(1-334)-linker(335-349)-H7 type HA1(350-572) with glycine/serine linker peptide to express one protein. In order that the linked peptides are effectively decoded in eukaryotic cells or *E. coli*, and can be used for identification and separation of proteins expressed on the carboxy terminal side of the linked peptide amino acids, peptides that act as flag tags (DYKDDDDKG) and His tags (HHHHHH) are linked to design a protein composed of a total of 587 amino acids (FIG. 1 and SEQ ID NO: 1).

In order to prepare a recombinant virus expressing the protein as produced in animal cells, the codon nucleotide sequence corresponding to the amino acid sequence of this protein was determined by optimizing the codon in a form that can be read best in animal cells. Finally, a gene expressing the fusion protein was synthesized by adding the RBS/Kozak nucleotide sequence, which is a ribosome binding site that helps protein decoding in front of the entire nucleotide sequence (RBS KOZAK/HA1(H5) (1-346; SEQ ID NO: 2)/GS linker(15)/HA1(H7)(17-339; SEQ ID NO: 3)/FLAG/His6tga)(SEQ ID NO: 4). Gene synthesis was performed using Cosmo Genetech's gene synthesis service.

<Example 2> Expression of H5 Type and H7 Type HA1 Fusion Protein

In order to confirm the production of the fusion protein from the gene produced as described above, the synthesized gene was inserted into a eukaryotic expression vector to produce a recombinant adenovirus particle containing the expression vector. To produce fusion protein gene, firstly, a pAd5-AI #4212 clone inserted in a direction in which the gene can be transcribed between the CMV promoter of the pShuttle-CMV shuttle vector and the SV40 polyA site, required for the production of recombinant adenovirus was obtained (FIG. 2).

The pAd5-AI #4212 DNA was investigated by Genuine Tech Co., Ltd. to confirm that the fusion protein can be produced in animal cells using recombinant adenovirus particles containing this plasmid. To this end, $2\times10^5$ HEK293A cells were cultured overnight, and then $2\times10^9$ pfu of pAd5-AI #4212 recombinant adenovirus particles were mixed in the culture solution so that the MOU became 10,000, and the cells were infected, and then incubated for 24 hours in a medium containing fetal bovine serum. Thereafter, the medium was replaced with a medium without fetal bovine serum, and then cultured for 24 hours, and then the culture medium was collected. In this way, the culture medium of the infected cells was collected three times to recover the fusion protein. The culture medium containing the collected fusion protein was concentrated 20-fold, and then the production of fusion protein was investigated by a western blotting method using a Flag tag. As a control, a recombinant adenovirus expressing green fluorescent protein (GFP) was used instead of the fusion protein. The concentrated culture was separated by SDS-PAGE, and the protein was transferred to the NC Membrane, reacted with a mouse anti-Flag antibody, and then reacted with a secondary antibody, Rat-anti-mouse IgG1-HRP (eBioscience). After the reaction was completed, the reaction was washed with PBS and then reacted with WEST-Queen™ kit (iNtRON), and the presence or absence of the protein reacting with the Flag tag antibody and its size was measured using a fluorescence image analyzer (Fusion-SL4) (FIG. 3). As a result, proteins that react with the Flag tag antibody were not identified in the cell culture medium infected with GFP-expressing recombinant adenovirus used as a control, but in the cell culture medium infected with the recombinant adenovirus expressing the fusion protein (pAd5-AI #4212 adenovirus), it was found that 50 kDa and 100 kDa proteins reacted with the Flag tag antibody. These results show that the expression construct produces a successfully fused protein from the produced H5 type HA1 and H7 type HA1 fusion proteins.

<Example 3> Effect of Inducing Antibody Production by Recombinant Adenovirus Expressing H5 and H7 Types HA1 Fusion Proteins in Mice Four five-week-old female BALB/c mice were inoculated with pAd5-AI #4212 recombinant adenovirus particles expressing H5 type and H7 type HA1 fusion protein by intranasal instillation. As a control, 4 mice were inoculated with a recombinant adenovirus expressing green fluorescent protein (GFP) instead of the fusion protein by intranasal inhalation. For intranasal inhalation, 5×10⁸ pfu recombinant adenovirus particles were diluted in 30 μl of a phosphate buffer solution and 5 μl of each was alternately inhaled using both nose holes. After the completion of the first inoculation and breeding for 3 weeks, and then the virus was inoculated again in the same manner. One week after the inoculation, blood was collected from the eyes of mice to prepare antisera.

The presence or absence of antibody against the fusion protein in the serum obtained by inoculating a recombinant adenovirus expressing the fusion protein twice by intranasal inhalation was confirmed using Enzyme-linked ImmunoSorbent Assay (ELISA). First, the H5 type and H7 type HA1 fusion protein culture solution obtained from cell culture were added to the ELISA plate and reacted overnight at 4° C. to coat the fusion protein. The next day, the serum of the mice inoculated with the fusion protein recombinant adenovirus was diluted 500 times and reacted for 2 hours at room temperature, and then reacted with the HRP-conjugated anti-mouse IgG/M secondary antibody (Merck Millipore AP130P) and antigen-antibody reaction was measured at 450 nm with an ELISA leader (ThermoFisher MULTISKAN GO). As a result, it was confirmed that antibodies reacting with the fusion protein were formed in the serum of mice inhaled with the recombinant adenovirus expressing the H5 type and H7 type HA1 fusion proteins (FIG. 4).

These results show that the recombinant adenovirus expressing the H5 type and H7 type HA1 fusion proteins was infected in the respiratory mucosa like a normal adenovirus, and the antibody response was induced in the mouse immune system in a similar manner as when infected with the influenza virus. In other words, it is suggested that the recombinant adenovirus having the HA fusion protein gene of the influenza virus can be effectively infected in the respiratory tract of an animal to be used as a live vaccine that effectively induces an immune response to the inserted influenza protein. Influenza vaccine using this type of fusion protein is a multivalent vaccine that simultaneously provides two or more influenza antigens to the immune system and it is a new preparation method of influenza vaccine that has not been attempted at all so far. These vaccines offer several advantages over multivalent vaccines using a mixture of several types of influenza viruses.

The multivalent influenza live vaccine platform in which multiple antigens are bound to one recombinant viral particle as the present invention does not require the process of producing and mixing each monovalent vaccine virus, so it is expected to be able to quickly respond to avian influenza transmission. Also, because recombinant adenovirus is a live virus, it can induce a strong immune response against influenza virus as in AI virus infection and it is a live attenuated vaccine, it can be easily administered by respiratory inhalation like influenza virus infection, and mass vaccination is possible, and it is a vaccine manufacturing method suitable for poultry vaccination. In addition, since recombinant adenovirus is a relatively harmless virus and does not use highly pathogenic influenza virus for vaccine production, the risk of biosafety in the manufacturing process is low, and it will further contribute to shorten the production period and to reduce the production cost.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

The invention claimed is:

1. A recombinant fusion protein of influenza A virus H5 type hemagglutinin 1 (HA1) and H7 type HAL which is obtained from a recombinant adenovirus strain transfected with a recombinant expression vector comprising an influenza A virus H5 type hemagglutinin 1 (HA1) gene and an influenza A virus H7 type HA1 gene.

2. The recombinant fusion protein of claim 1, wherein the recombinant expression vector comprises a ribosome binding site, an influenza A virus H5 type HA1 gene, a linker, an influenza A virus H7 type HA1 gene and a tag gene in order.

3. The recombinant fusion protein of claim 1, wherein the influenza A virus H5 type HA1 gene is represented by SEQ ID NO: 2, and the influenza A virus H7 type HA1 gene is represented by SEQ ID NO: 3.

4. The recombinant fusion protein of claim 1, wherein the recombinant fusion protein is represented by SEQ ID NO: 1.

5. A method of preparing recombinant adenovirus particles comprising:

transfecting adenovirus with a recombinant expression vector comprising an influenza virus H5 type HA1 gene and an influenza virus H7 type HA1 gene; and
culturing transfected adenovirus.

6. The method of preparing recombinant adenovirus particles of claim 5, wherein the recombinant adenovirus particles express influenza virus H5 type HA1 and H7 type HA1 recombinant fusion proteins.

7. The method of preparing recombinant adenovirus particles of claim 6, wherein the recombinant fusion protein is represented by SEQ ID NO: 1.

8. A method of treating influenza, comprising:
providing a vaccine composition comprising the recombinant fusion protein of claim 1 as an active ingredient; and
administering the vaccine composition to a subject.

9. The method of treating influenza of claim 8, wherein the influenza is avian influenza, swine influenza or human influenza.

* * * * *

```
                    SEQUENCE LISTING

<160> NUMBER OF SEQ ID NOS: 4

<210> SEQ ID NO 1
<211> LENGTH: 699
<212> TYPE: PRT
<213> ORGANISM: Artificial Sequence
<220> FEATURE:
<223> OTHER INFORMATION: fusion protein

<400> SEQUENCE: 1

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asn Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Ser Pro Ala Asn Asp Leu Cys Tyr Pro Gly Asp Phe Asn
            100                 105                 110

Asp Tyr Glu Glu Leu Lys His Leu Leu Ser Arg Thr Asn His Phe Glu
        115                 120                 125
```

```
Lys Ile Gln Ile Ile Pro Lys Ser Ser Trp Ser Asn His Asp Ala Ser
130                 135                 140

Ser Gly Val Ser Ser Ala Cys Pro Tyr His Gly Arg Ser Ser Phe Phe
145                 150                 155                 160

Arg Asn Val Val Trp Leu Ile Lys Lys Asn Ser Ala Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
    210                 215                 220

Leu Val Pro Glu Ile Ala Thr Arg Pro Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Thr
                325                 330                 335

Pro Gln Arg Glu Arg Arg Arg Lys Lys Arg Gly Gly Gly Gly Ser Gly
            340                 345                 350

Gly Gly Gly Ser Gly Gly Gly Ser Asn Ala Asp Lys Ile Cys Leu
        355                 360                 365

Gly His His Ala Val Ser Asn Gly Thr Lys Val Asn Thr Leu Thr Glu
    370                 375                 380

Arg Gly Val Glu Val Val Asn Ala Thr Glu Thr Val Glu Arg Thr Asn
385                 390                 395                 400

Val Pro Arg Ile Cys Ser Lys Gly Lys Arg Thr Val Asp Leu Gly Gln
                405                 410                 415

Cys Gly Leu Leu Gly Thr Ile Thr Gly Pro Pro Gln Cys Asp Gln Phe
            420                 425                 430

Leu Glu Phe Ser Ala Asp Leu Ile Ile Glu Arg Arg Glu Gly Ser Asp
        435                 440                 445

Val Cys Tyr Pro Gly Lys Phe Val Asn Glu Glu Ala Leu Arg Gln Ile
    450                 455                 460

Leu Arg Glu Ser Gly Gly Ile Asp Lys Glu Thr Met Gly Phe Thr Tyr
465                 470                 475                 480

Ser Gly Ile Arg Thr Asn Gly Ala Thr Ser Ala Cys Arg Arg Ser Gly
                485                 490                 495

Ser Ser Phe Tyr Ala Glu Met Lys Trp Leu Leu Ser Asn Thr Asp Asn
            500                 505                 510

Ala Ala Phe Pro Gln Met Thr Lys Ser Tyr Lys Asn Thr Arg Lys Asp
        515                 520                 525

Pro Ala Leu Ile Ile Trp Gly Ile His His Ser Gly Ser Thr Thr Glu
    530                 535                 540
```

```
Gln Thr Lys Leu Tyr Gly Ser Gly Asn Lys Leu Ile Thr Val Gly Ser
545                 550                 555                 560

Ser Asn Tyr Gln Gln Ser Phe Val Pro Ser Pro Glu Ala Arg Pro Gln
                565                 570                 575

Val Asn Gly Gln Ser Gly Arg Ile Asp Phe His Trp Leu Met Leu Asn
            580                 585                 590

Pro Asn Asp Thr Val Thr Phe Ser Phe Asn Gly Ala Phe Ile Ala Pro
        595                 600                 605

Asp Arg Ala Ser Phe Leu Arg Gly Lys Ser Met Gly Ile Gln Ser Gly
    610                 615                 620

Val Gln Val Asp Ala Asn Cys Glu Gly Asp Cys Tyr His Ser Gly Gly
625                 630                 635                 640

Thr Ile Ile Ser Asn Leu Pro Phe Gln Asn Ile Asn Ser Arg Ala Val
                645                 650                 655

Gly Lys Cys Pro Arg Tyr Val Lys Gln Glu Ser Leu Leu Leu Ala Thr
                660                 665                 670

Gly Met Lys Asn Val Pro Glu Ile Pro Lys Gly Arg Asp Tyr Lys Asp
            675                 680                 685

Asp Asp Asp Lys Gly His His His His His His
    690                 695

<210> SEQ ID NO 2
<211> LENGTH: 1038
<212> TYPE: DNA
<213> ORGANISM: Artificial Sequence
<220> FEATURE:
<223> OTHER INFORMATION: influenza virus H5 type HA1

<400> SEQUENCE: 2
atggagaaga ttgtcctcct tctcgcaatc gtgtcactgg ttaagagtga tcaaatctgt     60
atcggttacc acgcaaataa ctcaactgag caagtcgata caattatgga gaaaaatgtg    120
acagtcaccc atgctcaaga cattctcgag aagactcaca cggcaagct gtgcgatctc     180 aacggcgtta accattgat attgagggat tgttccgtag cgggatggtt gctcggtaat    240
ccgatgtgcg atgaattcat caatgtccct gagtggagtt acatagtgga aaaggcctca    300
ccggcaaacg atctctgcta tcccggcgac ttcaatgatt atgaagaatt gaagcatttg    360
ctctccagga cgaaccattt cgaaaagatc cagatcatcc caaaagctc ttggagcaac    420 cacgacgcaa gcagtgggt cagctcagct tgtccttacc acggacgctc ctccttcttt    480
cgcaatgtag tatggctgat taagaaaaat agcgcgtacc caaccatcaa agaagttat    540 aataacacga tcaggagga tcttttggtg ctttggggga ttcatcatcc aatgacgcg    600 gccgaacaga ccaagttgta ccaaaacccc accacctaca tcagcgtcgg cacctctact    660
ctgaatcaac gcttggtccc tgaaatagca accagaccaa aggtaaatgg ccaatcaggt    720
cgcatggaat ttttctggac gatcctcaag cctaacgacg cgataaattt cgaatctaac    780
ggcaatttca tagcccccga atacgcttac aagattgtca aaaaggcga tagcgcaatc    840 atgaagtccg aactggagta tggtaactgc aatactaagt gccaaacccc gatgggagcc    900
ataaatagta gcatgccgtt tcataatatt catccgctga caattggtga gtgtccaaag    960
tacgttaaat ccaatcgcct cgtgttggcg acaggcttgc ggaacacacc tcagcgggag   1020
cggcggagaa aaaagcgc                                                 1038

<210> SEQ ID NO 3
<211> LENGTH: 969
```

```
<212> TYPE: DNA
<213> ORGANISM: Artificial Sequence
<220> FEATURE:
<223> OTHER INFORMATION: influenza virus H7 type HA1

<400> SEQUENCE: 3
aacgcggata agatttgctt gggccaccat gccgtgtcca atgggactaa ggtaaacaca      60
ttgaccgaaa ggggcgttga ggttgtaaat gcgaccgaga ctgtagaaag gacgaatgtc     120
ccgcggatat gctctaaggg caaaaggacg gttgacctgg gtcaatgcgg tttgcttggt     180
acgatcacag gccgccccca atgtgatcaa ttcctggagt tttctgccga ccttataatc     240
gaacgcaggg agggttccga tgtctgttat ccaggtaaat ttgtcaatga ggaggctctc     300
aggcaaatac tccgcgagtc cggaggaata gacaaggaaa ctatgggatt tacatattct     360
ggcattcgaa ccaacggagc tacatccgca tgtcgccggt ccggtagctc attttacgct     420
gagatgaaat ggctcttgag caacacagac aatgccgcgt tccccaaat gacgaagtcc      480
tacaaaaaca ctagaaaaga tcctgcgctc attatctggg gcattcatca tagcggttca     540
accaccgaac agacgaaact ttatggcagc ggaaataaac tgatcaccgt cggctcatca     600
aattatcagc agtcttttgt gccatcccca gaggcaagac acaggtgaa cggccaatct      660
gggcgaatcg attttcattg gcttatgctg aaccctaacg acactgtcac ttttctttc      720
aatggagctt ttatagcacc agacagagcc agcttcctca gaggcaaatc tatgggcata     780
cagtctggtg tgcaggtaga cgccaattgt gagggagatt gttatcactc aggggggtaca    840
atcatctcaa atctgccttt tcagaatata aatagccggg cagttggcaa gtgcccaaga     900
tacgttaagc aggaaagtct cttgctggca acaggcatga aaaacgtccc agagatcccg     960
aaaggcaga                                                             969

<210> SEQ ID NO 4
<211> LENGTH: 2115
<212> TYPE: DNA
<213> ORGANISM: Artificial Sequence
<220> FEATURE:
<223> OTHER INFORMATION: influenza virus fusion gene

<400> SEQUENCE: 4
aaggaggccg ccaccatgga aagattgtc ctccttctcg caatcgtgtc actggttaag       60
agtgatcaaa tctgtatcgg ttaccacgca ataactcaa ctgagcaagt cgatacaatt     120
atggagaaaa atgtgacagt cacccatgct caagacattc tcgagaagac tcacaacggc    180
aagctgtgcg atctcaacgg cgttaaacca ttgatattga gggattgttc cgtagcggga    240
tggttgctcg gtaatccgat gtgcgatgaa ttcatcaatg tccctgagtg gagttacata    300
gtggaaaagg cctcaccggc aaacgatctc tgctatcccg cgacttcaa tgattatgaa    360
gaattgaagc atttgctctc caggacgaac catttcgaaa agatccagat catccccaaa    420
agctcttgga gcaaccacga cgcaagcagt ggggtcagct cagcttgtcc ttaccacgga    480
cgctcctcct tctttcgcaa tgtagtatgg ctgattaaga aaaatagcgc gtacccaacc    540
atcaaaagaa gttataataa cacgaatcag gaggatcttt ggtgctttg ggggattcat     600
catcccaatg acgcggccga acagaccaag ttgtaccaa accccaccac ctacatcagc    660
gtcggcacct ctactctgaa tcaacgcttg gtccctgaaa tagcaaccag accaaaggta    720
aatggccaat caggtcgcat ggaatttttc tggacgatcc tcaagcctaa cgacgcgata    780
aatttcgaat ctaacggcaa tttcatagcc cccgaatacg cttacaagat tgtcaaaaaa    840
```

-continued

```
ggcgatagcg caatcatgaa gtccgaactg gagtatggta actgcaatac taagtgccaa    900
accccgatgg gagccataaa tagtagcatg ccgtttcata atattcatcc gctgacaatt    960
ggtgagtgtc caaagtacgt taaatccaat cgcctcgtgt tggcgacagg cttgcggaac   1020
acacctcagc gggagcggcg gagaaaaaag cgcggaggtg gcggttcagg cggaggaggt   1080
tccgggggag gcggctctaa cgcggataag atttgcttgg gccaccatgc cgtgtccaat   1140
gggactaagg taaacacatt gaccgaaagg ggcgttgagg ttgtaaatgc gaccgagact   1200
gtagaaagga cgaatgtccc gcggatatgc tctaagggca aaaggacggt tgacctgggt   1260
caatgcggtt tgcttggtac gatcacaggg ccgccccaat gtgatcaatt cctggagttt   1320
tctgccgacc ttataatcga acgcagggag ggttccgatg tctgttatcc aggtaaattt   1380
gtcaatgagg aggctctcag gcaaatactc cgcgagtccg gaggaataga caaggaaact   1440
atgggattta catattctgg cattcgaacc aacggagcta catccgcatg tcgccggtcc   1500
ggtagctcat tttacgctga gatgaaatgg ctcttgagca acacagacaa tgccgcgttt   1560
ccccaaatga cgaagtccta caaaaacact agaaaagatc ctgcgctcat tatctggggc   1620
attcatcata gcggttcaac caccgaacag acgaaacttt atggcagcgg aaataaactg   1680
atcaccgtcg gctcatcaaa ttatcagcag tcttttgtgc catccccaga ggcaagacca   1740
caggtgaacg gccaatctgg gcgaatcgat tttcattggc ttatgctgaa ccctaacgac   1800
actgtcactt tttcttttcaa tggagctttt atagcaccag acagagccag cttcctcaga   1860
ggcaaatcta tgggcataca gtctggtgtg caggtagacg ccaattgtga gggagattgt   1920
tatcactcag ggggtacaat catctcaaat ctgcctttc agaatataaa tagccgggca   1980
gttggcaagt gcccaagata cgttaagcag gaaagtctct tgctggcaac aggcatgaaa   2040
aacgtcccag agatcccgaa aggcagagac tataaggatg acgacgataa aggacatcat   2100
caccatcatc actga                                                    2115
```